United States Patent
Eldar et al.

(10) Patent No.: US 7,290,011 B2
(45) Date of Patent: Oct. 30, 2007

(54) IMAGE PUBLISHING SYSTEM USING PROGRESSIVE IMAGE STREAMING

(75) Inventors: Adi Eldar, Kiryat Ono (IL); Laurence Keselbrener, Tel Aviv (IL)

(73) Assignee: IDX Investment Corporation, Burlington, VT (US)

( * ) Notice: Subject to any disclaimer, the term of this patent is extended or adjusted under 35 U.S.C. 154(b) by 403 days.

(21) Appl. No.: 10/723,404

(22) Filed: Nov. 26, 2003

(65) Prior Publication Data

US 2005/0114380 A1    May 26, 2005

(51) Int. Cl.
 *G06F 17/00* (2006.01)
(52) U.S. Cl. ....................... 707/104.1; 705/2
(58) Field of Classification Search ............. 705/2; 709/207
See application file for complete search history.

(56) References Cited

U.S. PATENT DOCUMENTS

| | | | | |
|---|---|---|---|---|
| 5,291,401 | A * | 3/1994 | Robinson | 382/132 |
| 5,469,353 | A * | 11/1995 | Pinsky et al. | 382/131 |
| 6,260,021 | B1 * | 7/2001 | Wong et al. | 705/2 |
| 6,314,452 | B1 | 11/2001 | Dekel et al. | 709/203 |
| 6,500,122 | B1 | 12/2002 | Washburn et al. | 600/443 |
| 6,574,629 | B1 * | 6/2003 | Cooke, Jr. et al. | 707/10 |
| 6,678,764 | B2 * | 1/2004 | Parvulescu et al. | 710/65 |
| 2002/0016718 | A1 * | 2/2002 | Rothschild et al. | 705/2 |
| 2003/0005140 | A1 | 1/2003 | Dekel et al. | 709/231 |
| 2003/0059096 | A1 | 3/2003 | Dekel et al. | 382/131 |
| 2004/0141661 | A1 * | 7/2004 | Hanna et al. | 382/305 |
| 2006/0031372 | A1 * | 2/2006 | Krishnan et al. | 709/207 |

* cited by examiner

Primary Examiner—Apu Mofiz
Assistant Examiner—Paul Kim
(74) *Attorney, Agent, or Firm*—Zaretsky & Associates PC; Howard Zaretsky (57) ABSTRACT

An image publishing system provides a distribution mechanism whereby images are forwarded automatically to users in accordance with a set of publication rules. The rules determine which images are to be sent to which users. The images are forwarded to users as they become available on an image archive storage device. This overcomes the requirement of users having to manually request the transmission of each individual image they would like to view. Progressive image streaming techniques employing compression are used to transmit images in encoded layers of increasing accuracy and quality. Means is also provided permitting users to view any image queued for transmission at a publication server, regardless of how much of the image has been received by a client computer. This allows images whose data transmission has not even begun yet to be viewed by a user. A user interrupts the normal background process at any time and requests to view a particular image. If the required data is not found locally, it is requested form the publication server and given high priority. The requested data is received, decoded and immediately displayed to the user.

28 Claims, 9 Drawing Sheets

IMAGE PUBLISHING SYSTEM USING PROGRESSIVE IMAGE STREAMING

FIELD OF THE INVENTION

The present invention relates to systems and methods for the transmission of images over communication networks and more particularly relates to an image publishing system and method that utilizes progressive image streaming.

BACKGROUND OF THE INVENTION

Image publishing systems are widely used to distribute images from a centralized server computer connected to a network to users that are also connected to the network. The images are generated by an image source and stored in a centralized database connected to the server computer. Users at client computers make requests for images to the server computer. The server computer, in response to the requests, sends image data over the network to the user at the client computer.

Image publishing systems can be used in numerous fields and disciplines including, for example, the medical field. The image publishing systems used by the medical field, and particularly hospitals, utilize specialized hardware and software to store, distribute and view medical related image data. A medical image publishing system is termed a Picture Archiving and Communication System (PACS).

A typical PACS system includes one or more imaging sources, an archive or image database and multiple viewing stations. Typical image sources include X-ray, computerized tomography (CT) scans, nuclear medicine images, ultrasound and magnetic resonance imaging (MRI). The images, once generated, are stored on a centralized storage device. Users can then request to view the images on their viewing stations. Requested images first have to be located in the archive, retrieved and transmitted to the user's client computer.

Users are typically connected to the PACS server computer over a communications network. The network may be a local area network (LAN) or a wide area network (WAN) such as the Internet. Currently, the data rate for a typical LAN network connection is relatively fast, e.g., 100 Mbps using Fast Ethernet (FE). Even higher data rates of Gigabit Ethernet (GE) at 1 Gbps are becoming increasingly common in LANs. WAN connections, however, typically have much slower data rates. Although high data rate WAN connections, e.g., broadband connections, are becoming increasingly common, many users still communicate over slow speed WAN connections, e.g., 64 kbps or less using modems.

Since typical medical images, e.g., radiological images, are relatively large files, e.g., tens of megabytes, it would take a relatively long time to transmit entire images to users located remotely from the centralized PACS server and connected using slow speed communications.

A disadvantage of a conventional PACS system is that image distribution is performed manually. An image source generates an image where it is stored on an image archive or storage facility connected to the server. Once it is stored, a user, e.g., physician, at a viewing station or client computer must manually request to view the image. The client computer generates a request and sends it to the PACS server. In response to the request, the server retrieves the image from the image database and transmits it to the client computer. A problem arises in that many times, users do not know when an image becomes available for viewing. There is typically a lag between the time when the image is actually available and the time when the user is aware of this fact and requests the image to be transferred. This is inefficient in terms of time since a physician, for example, would typically like to be able to view the images as soon at they are available.

A further disadvantage is that a conventional PACS system requires a user to wait until the entire image is successfully received before the image can be viewed. In the case of an emergency, a physician would not want to wait for the radiology images to be transmitted in their entirety from a PACS server.

The problems discussed above are compounded when considering that in the medical field, physicians work with radiological studies and not with individual images. A study is a collection of data comprising anything that may be useful to the physician viewing the data. Examples of the contents of studies include one or more radiological images (CT scan, MRI, ultrasound, etc. of various body parts), text files containing medical histories, medical opinions from other physicians, laboratory test results, etc.

Conventional PACS systems perform medical image transfer by sending the entire study data from the image storage location to the user's client workstation. Depending on bandwidth availability, and compression ratios, this may take hours to complete over a slow network connection, e.g., dial-up line, creating a tradeoff between speed of delivery and degree of image quality. Further, the contents of a study cannot be viewed until the entire study is completely received by the client computer or viewing station. In the case of a large study, this is inefficient and undesirable because the physician must wait for the entire contents of a study to be received before being able to view any of the images within the study.

Therefore, there is a need for an image publishing system with improved distribution over slow WAN communication connections. It is desirable that such a system provides some form of data pushing whereby studies (or images) are immediately sent to users automatically once they become available on the server. It is also desirable that the image publishing system has the capability of overcoming the limitation imposed by slow WAN connections. It is further desirable that the image publishing system permits users to view the contents of a study or image before data transmission for that study or image is complete.

SUMMARY OF THE INVENTION

The present invention provides an image publishing system that overcomes the problems of the prior art. The system comprises a distribution mechanism whereby images are forwarded automatically to users in accordance with a set of publication rules. The rules determine which images are to be sent to which users. The images are forwarded to users as they become available on an image archive storage device. This overcomes the requirement of users having to manually request the transmission of each individual image they would like to view.

The system also has the capability of overcoming the limitation imposed by slow WAN communication connections. Progressive image streaming techniques employing compression are used to transmit images in encoded layers of increasing accuracy and quality.

The system also permits users to view any image that is queued up for transmission at the server, regardless of how much of the image has been received by the client computer. Thus, even images whose data transmission has not even begun yet may be viewed by a user. Normally, images are sent, in either a pull or a push mode of data transmission, from the server computer to a client computer as a background process with no intervention required by the user. However, a user may at any time during this process, interrupt the normal background process and request to view a particular image. The invention first utilizes any data that has already been received by the client computer. If the required data is not available on the client computer, the data is pulled from the server using progressive image streaming techniques. The data is received, decoded and immediately displayed to the user.

Thus, the invention functions to combine the advantages of progressive image streaming with an interactive capability where studies not yet received can be immediately viewed since the publication server transmits a first progressive layer that is a highly compressed/low quality approximation of the image while the last layer is the lossless layer. Once in the interactive mode, the user can view any part of the image. Requests for regions of interest are generated and sent by the client computer to the publication server. The requests are given high priority while the background task of retrieving study for the other non-selected studies continues. Depending on the available bandwidth and the requests by the user, data reception for the non-selected studies may slow down or stop altogether. The user can quit the interactive mode at any time whereby the task of retrieving data for all the queued studies continues. Any data already received for a selected study viewed in interactive mode is not transmitted again from the publication server.

An image publishing system software product embodying the systems and methods of the present invention is available commercially as the iPACS family of products manufactured by RealTimeImage, San Bruno, Calif. Using the systems and methods of the present invention, the iPACS product permits medical personnel to share images immediately and with lossless quality over any Web connection using a standard PC regardless of available bandwidth.

Note that many aspects of the invention described herein may be constructed as software objects that are executed in embedded devices as firmware, software objects that are executed as part of a software application on either an embedded or non-embedded computer system running a real-time operating system such as WinCE, Symbian, OSE, Embedded LINUX, etc. or non-real time operating system such as Windows, UNIX, LINUX, etc., or as soft core realized HDL circuits embodied in an Application Specific Integrated Circuit (ASIC) or Field Programmable Gate Array (FPGA), or as functionally equivalent discrete hardware components.

There is thus provided in accordance with the invention, a system for publishing images over a communication network comprising a study storage device for storing a plurality of studies, each study comprising one or more images, a publication server coupled to the communications network, the publication server adapted to enter an automatic mode wherein one or more studies are automatically sent to a client computer coupled to the communications network as they become available on the study storage device, the client computer adapted to receive the one or more studies and store them in a local storage and the client computer comprising means for a user to enter an interactive mode wherein a viewing session is initiated for viewing a selected study before transmission of the selected study is complete, wherein data for viewing the selected study is obtained from the publication server using progressive image streaming techniques and from data already received and stored in the local storage.

There is also provided in accordance with the invention, an image publication system for use on a client computer coupled to a communications network comprising first means for receiving a first command from a user to enter an automatic mode whereby new studies are sent immediately from the publication server to the client computer over the communications network as they become available, local storage device for storing the studies upon receipt, second means for receiving the studies and for storing them in the local storage, third means for receiving a second command from the user to view a selected study before data is completely received for the selected study and in response thereto, entering an interactive mode whereby an attempt is made to obtain data required for viewing the selected study from the local storage, and if unsuccessful, from the publication server using progressive image streaming techniques via one or more requests transmitted from the client computer to the publication server and fourth means for receiving and decoding data received from the publication server in response to the one or more requests.

There is further provided in accordance with the invention, an image publication system for use on a publication server computer coupled to a communications network comprising first means for receiving instructions from a client computer coupled to the communications network, the first means for configuring the publication server computer to automatically send new studies to the client computer as the studies become available, second means for receiving requests for specific layers of accuracy for regions of interest of a study selected by a user for viewing on the client computer before transmission of data for the selected study is complete and third means for sending the specific layers of accuracy for regions of interest of the selected study to the client computer in response to the requests.

There is also provided in accordance with the invention, a computer program product for use in a client computer coupled to a communication network, the computer program product comprising a computer readable medium having computer readable program code means embodied in the medium for receiving and displaying studies from a publication server coupled to the communications network, the computer program product comprising computer readable program code means for receiving a first command from a user to enter an automatic mode whereby new studies are sent immediately from the publication server to the client computer over the communications network as they become available, computer readable program code means for receiving the studies and for storing them in a local storage device coupled to the client computer, computer readable program code means for receiving a second command from the user to view a selected study before its data is completely received and in response thereto, entering an interactive mode whereby data required for viewing the selected study is first obtained from the local storage, and if unsuccessful, from the publication server using progressive image streaming techniques via one or more requests transmitted from the client computer to the publication server and computer readable program code means for receiving and decoding data received from the publication server in response to the one or more requests.

There is further provided in accordance with the invention, a computer program product for use in a publication server computer coupled to a communication network, the computer program product comprising a computer readable medium having computer readable program code means embodied in the medium for publishing studies to a client computer coupled to the communications network, the computer program product comprising computer readable program code means for receiving instructions from the client computer and for configuring the publication server computer to automatically send new studies to the client computer as the studies become available on a study database coupled to the publication server computer, computer readable program code means for receiving requests for specific layers of accuracy for regions of interest of a study selected by a user for viewing on the client computer before transmission of data for the selected study is complete and computer readable program code means for sending the specific layers of accuracy for regions of interest of the selected study to the client computer in response to the requests.

BRIEF DESCRIPTION OF THE DRAWINGS

The invention is herein described, by way of example only, with reference to the accompanying drawings, wherein.

DETAILED DESCRIPTION OF THE INVENTION

Notation Used Throughout

The following notation is used throughout this document.

| Term | Definition |
| --- | --- |
| ASIC | Application Specific Integrated Circuit |
| CD-ROM | Compact Disk-Read Only Memory |
| CPU | Central Processing Unit |
| CR | Computed Radiography (digital X-ray image) |
| CT | Computerized Tomography |
| DAT | Digital Audio Tape |
| DSP | Digital Signal Processor |
| DVD | Digital Versatile Disk |
| EEPROM | Electrically Erasable Programmable Read Only Memory |
| EEROM | Electrically Erasable Read Only Memory |
| EPROM | Electrically Programmable Read Only Memory |
| FE | Fast Ethernet |
| FPGA | Field Programmable Gate Array |
| GE | Gigabit Ethernet |
| IEEE | Institute of Electrical and Electronic Engineers |
| LAN | Local Area Network |
| MAN | Metropolitan Area Network |
| MRI | Magnetic Resonance Imaging |
| NIC | Network Interface Card |
| NVRAM | Non-Volatile Random Access Memory |
| OS | Operating System |
| PACS | Picture Archiving and Communication System |
| PC | Personal Computer |
| RAM | Random Access Memory |
| ROI | Region of Interest |
| ROM | Read Only Memory |
| UID | Unique ID |
| US | Ultrasound |
| WAN | Wide Area Network |

DETAILED DESCRIPTION OF THE INVENTION

The present invention provides an image publishing system that overcomes the disadvantages and problems of the prior art. The system comprises a distribution mechanism whereby images are forwarded automatically to users in accordance with a set of publication rules. The rules determine which images are to be sent to which users. The images are forwarded to users as they become available on an image archive storage device. This overcomes the requirement of users having to manually request the transmission of each individual image they wish to view.

The system also has the capability of overcoming the limitation imposed by slow WAN communication connections. Progressive image streaming techniques employing compression are used to transmit images in encoded layers of increasing accuracy and quality.

The system also permits users to view any image that is queued up for transmission at the server, regardless of how much of the image has been received by the client computer. Thus, even images whose data transmission has not even begun yet may be viewed by a user. Normally, images are sent, in either a pull or a push mode of data transmission, from the server computer to a client computer as a background process with no intervention required by the user. However, a user may at any time during this process, interrupt the normal background process and request to view a particular image. The invention first utilizes any data that has already been received by the client computer. If the required data is not available on the client computer, the data is pulled from the server using progressive image streaming techniques. The data is received, decoded and immediately displayed to the user.

The image publishing system of the present invention is applicable to a side variety of fields and disciplines such as medical imaging, teleradiology, graphic arts, printing, publishing, etc. For illustration purposes only, the present invention is described in the context of a medical imaging application. In particular, a PACS system used to store, distribute and view studies containing radiological images, text based reports, etc. It is appreciated by one skilled in the art that the invention is not limited to the example PACS system described herein but can be applied to numerous other fields and disciplines without departing from the spirit and scope of the invention. It is noted that the present invention is applicable in any system whereby data is distributed (or published) to a plurality of users and it is desirable to give users the ability to view any image queued for transmission before it has been completely received at a user's client computer. It is also noted that the present invention is not limited for use with any particular computer system, communication network, type or contents of study, image, etc., communications protocol, image format or progressive image streaming technique.

Throughout this document, the term study or study data is defined as a collection of data, such as about a patient. A study may contain images, text files or any other suitable data type for the particular application. The terms study and image may be used interchangeably even though a study may comprise other data in addition to images. The term study data is intended to denote any data that is typically relatively large in size such that transmission over low speed network connections would normally take hours.

Figure 1:
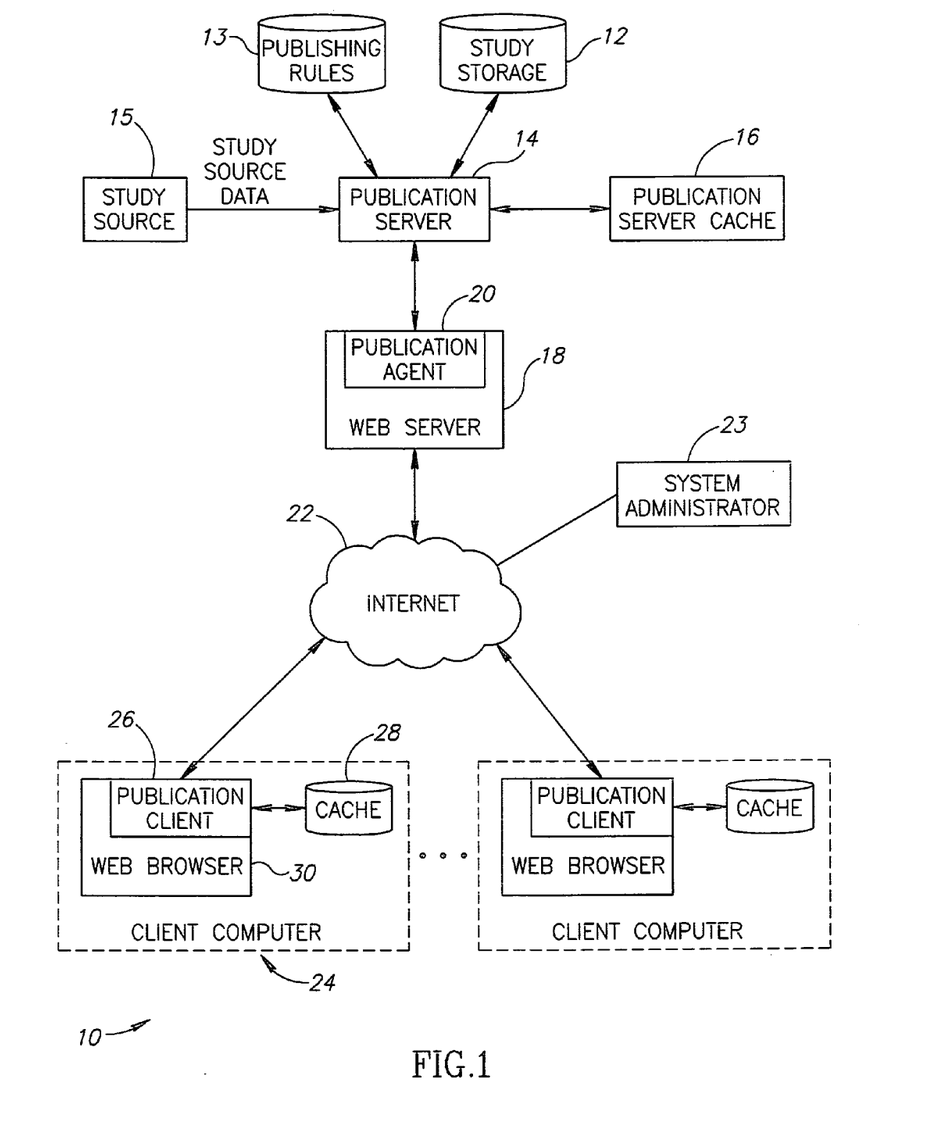
FIG. 1 is a block diagram illustrating an example network including server and client computers constructed in accordance with the principles of the present invention and connected to a wide area network such as the Internet.

A block diagram illustrating an example network including server and client computers constructed in accordance with the principles of the present invention and connected to a wide area network such as the Internet is shown in FIG. 1. The example network 10, comprises the various components of the image publishing system. The system comprises several portions including a server portion, communication network and client portion. The server portion comprises a publication server 14, study source 15, publishing rules 13, study storage 12, publication server cache 16 and web server 18. The system may also include a system administrator 23 in communication with the client computers and server computers via the communications network 22. The client portion comprises one or more client computers 24 comprising a web browser 30 with publication client 26 and cache 28. The client computers and web server 18 are in communication with each other and to other computers through a communications network 22 such as the Internet, Intranet, local area network (LAN), wide area network (WAN), metropolitan area network (MAN), wireless network, etc. It is appreciated by those skilled in the art that a variety of communication networks may be used to implement the present invention.

In operation, the publication server is adapted to receive study source data from the study source. The study data may comprise any number of images, text files or any other data that may be useful to medical personnel in caring for a patient. The publication server stores the study data in a study storage device 12 where it is archived for subsequent distribution to users. The publishing rules 13 are used by the publication server to determine which users get what studies. The rules provide the distribution instructions for automatic delivery of study data once it becomes available. Note that the automatic delivery of data may be achieved using either a pull or push mode of data retrieval. In pull mode, the publication rules are used only for permission to pull and the user has the ability to decide if the actual publication (i.e. pull) will occur. The publication cache 16 is fast temporary storage memory used by the publication server to distribute study data to users.

Depending on the actual implementation, the publication server distributes study data through a web server 18. The publication agent 20 functions to interface the publication server to the web server. Queries and requests for study data are received from users' client computers over the communications network and forwarded to the publication server via the publication agent for processing and preparation of a response.

The web browser in the client computer may comprise any browser type application (e.g., Netscape, Internet Explorer, etc.). The user of the client computer connects to the web server 18 or directly to the publication server via a publication client in the client computer. When a user requests to view a particular study, a request message is sent to the publication server requesting data for the region the user wishes to view. The study data (e.g., image data) is transmitted to the client computer where it is received by the publication client and stored in a local storage cache 28.

Figure 2:
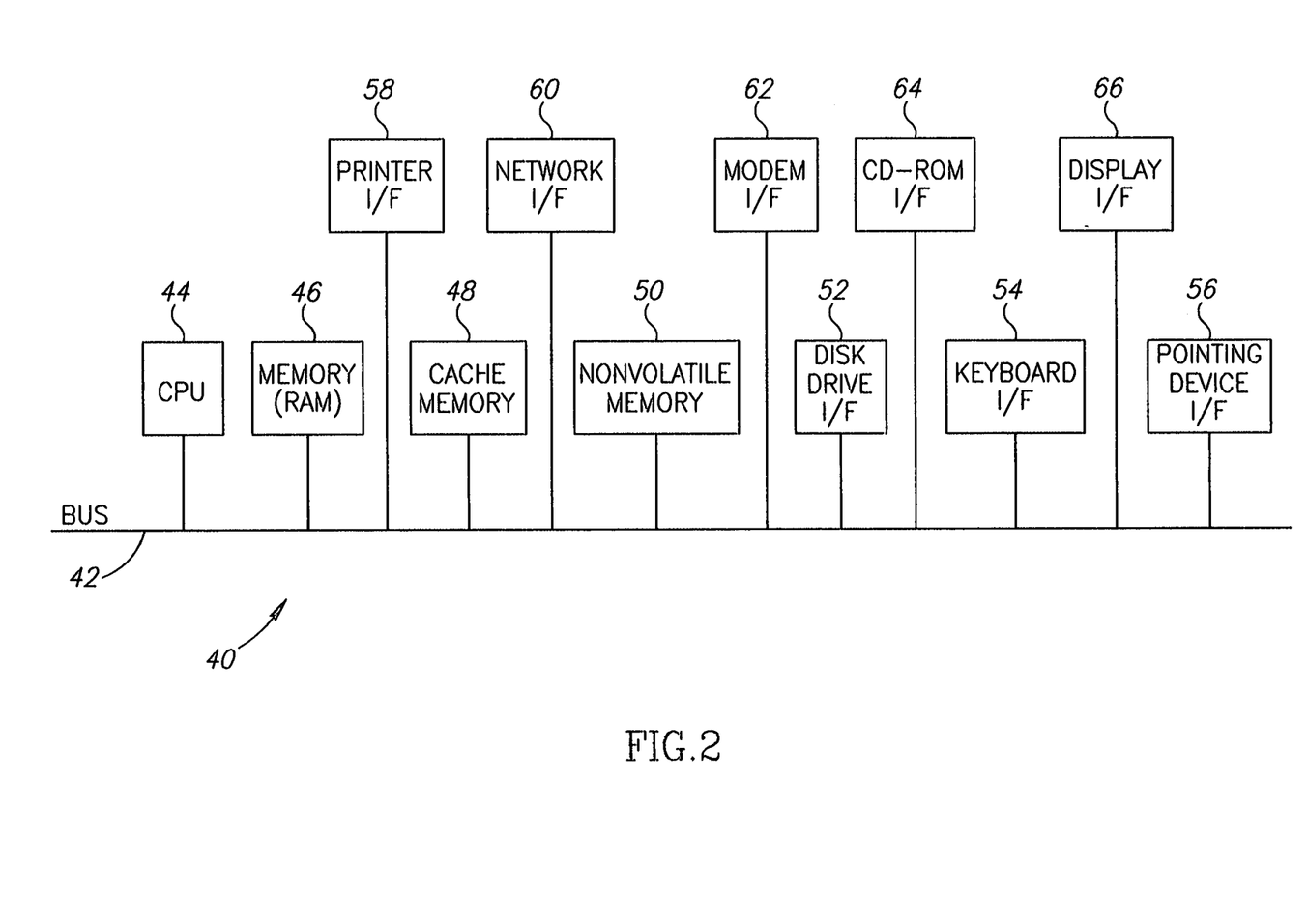
FIG. 2 is a block diagram illustrating the components of a computer adapted for use either as a client or server in accordance with the present invention.

A block diagram illustrating the components of a computer adapted for use either as a client or server in accordance with the present invention is shown in FIG. 2. The computer, generally referenced 40, may be used as either a server or client computer. The main components of the computer comprise a CPU 44 which may be implemented as a microcontroller, microprocessor, microcomputer, ASIC core, FPGA core, central processing unit (CPU) or digital signal processor (DSP), for example. The computer further comprises dynamic main memory 46 (e.g., RAM), fast cache memory 48, non-volatile RAM (NVRAM) 50 which may be static read only memory (ROM) and dynamic main memory (e.g., RAM) 46 all in communication with the CPU via a bus 42. The CPU is also in communication via the bus with a number of peripheral devices that are also included in the computer system.

The device is connected to a network, e.g., LAN, WAN, MAN, Internet, etc. via a network interface 60 (e.g., NIC) and/or modem interface 62. The network interface comprises wired and/or wireless interfaces to one or more communication channels. The network interface is adapted to handle the particular wired or wireless network protocol being used, e.g., one of the varieties of copper or optical Ethernet, Token Ring, IEEE 802.3b, 802.3a, etc.

The processor is also in communication, via the bus, with a number of peripheral devices that are also included in the computer system. Peripheral devices include one or more magnetic storage devices for storing application programs and data via disk drive interface 52, keyboard interface 54, pointing device interface 56, display interface 66, CD-ROM interface 64 and printer interface 58. The keyboard, pointing device and display form the user interface for inputting and responding to user inputs and to provide feedback and other status information. The system comprises computer readable storage medium which may include any suitable memory means including but not limited to magnetic storage, optical storage, CD-ROM drive, ZIP drive, DVD drive, DAT cassette, semiconductor volatile or non-volatile memory, biological memory devices, or any other memory storage device.

Software operative to implement the functionality of the image publishing system of the present invention or any portion thereof is adapted to reside on a computer readable medium, such as a magnetic disk within a disk drive unit or any other volatile or nonvolatile memory.

Alternatively, the computer readable medium may comprise a floppy disk, Flash memory card, EPROM, EEROM, EEPROM based memory, bubble memory storage, ROM storage, etc. The software being adapted to perform image publishing system of the present invention or any portion thereof may also reside, in whole or in part, in the static or dynamic main memories or in firmware within the processor of the computer system (i.e. within microcontroller, microprocessor, microcomputer, DSP, etc. internal memory).

In alternative embodiments, the method of the present invention may be applicable to implementations of the invention in integrated circuits, field programmable gate arrays (FPGAs), chip sets or application specific integrated circuits (ASICs), DSP circuits, wired or wireless implementations and other communication system products.

Figure 3:
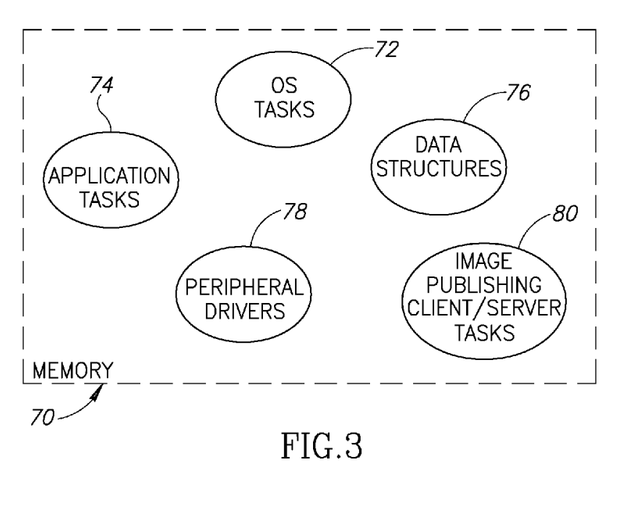
FIG. 3 is a block diagram illustrating the plurality of tasks adapted to execute on the computer of FIG. 2.

A block diagram illustrating the plurality of tasks adapted to execute on the computer of FIG. 2 is shown in FIG. 3. The memory, generally referenced 70, comprises a computer readable medium for the storage and execution of the software required to operate the computer and to implement the image publishing system of the present invention. The tasks shown are only a portion of the tasks required for the operation of the computer. For illustration purposes only, tasks shown include the tasks making up the operating system (OS) 72, application software tasks 74, the data structures 76 used in executing the software, peripheral driver software 78 and the image publishing tasks 80 for either client or server computer.

To aid in understanding the principles of the present invention, several sample display windows of the iPACS software mentioned supra are presented. The iPACS client/server software implements the image publishing system of the present invention. It is appreciated by one skilled in the art that the invention is not limited to the display windows presented herein and that any suitable display format, user interface design, display window design, etc. may be used with the invention.

Figure 4:
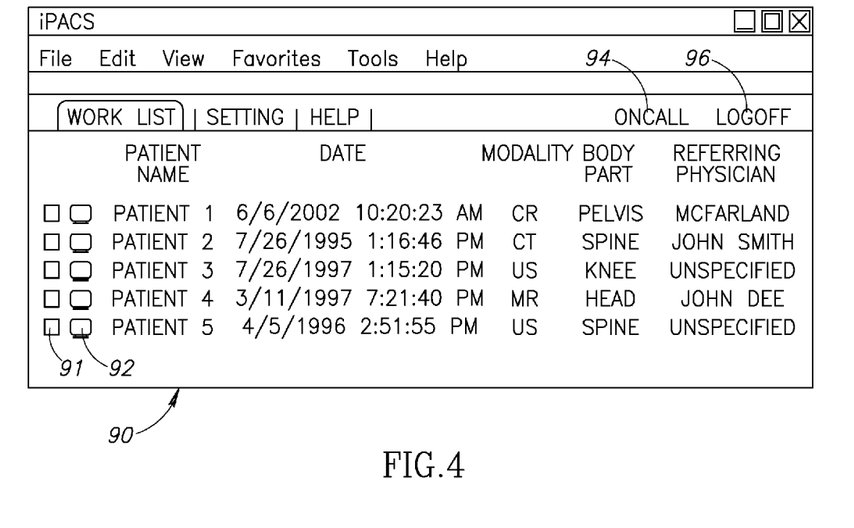
FIG. 4 is a diagram illustrating a sample window showing the contents of the Work List as generated by the software of the present invention.

A diagram illustrating a sample window showing the contents of the Studies Work List as generated by the software of the present invention is shown in FIG. 4. The display screen, generally referenced 90, shows one of the main displays of the iPACS client software application. A toolbar is provided as well as tabs for Work List, Settings and Help. In addition, OnCall 94 and Log Off 96 buttons are provided.

The Work List tab when selected, causes a list of all studies present in local storage on the client computer to be displayed. Alternatively, the Work List tab may be adapted to also display studies present on the publication server but not yet transmitted to the client computer. For each study, the following is displayed: a selection box 91, display icon 92 for viewing a study, patient name, date and time the study was created, the modality of the study, the body part and the referring physician. The modality information may include computed radiography or digital X-ray (CR), computerized tomography (CT), ultrasound (US) or magnetic resonance imaging (MR).

A key feature of the iPACS software is the OnCall button feature. When a user presses the OnCall button, the client computer enters the OnCall mode and the OnCall display window is opened. The OnCall mode is actually an automatic mode of operation for retrieving studies from the publication server as they become available without any intervention by a user. To configure the system for automatic transmission of studies, the publication rules are modified such that new studies that fit particular criteria are automatically sent to the particular user. The actual rules may be based on any suitable criteria and are not critical to operation of the invention. For example, the criteria may include the patient name, particular body part, particular referring physician, date, time, etc. The rules may be set statically a priori or they may be set dynamically by the user or system administrator.

Figure 5:
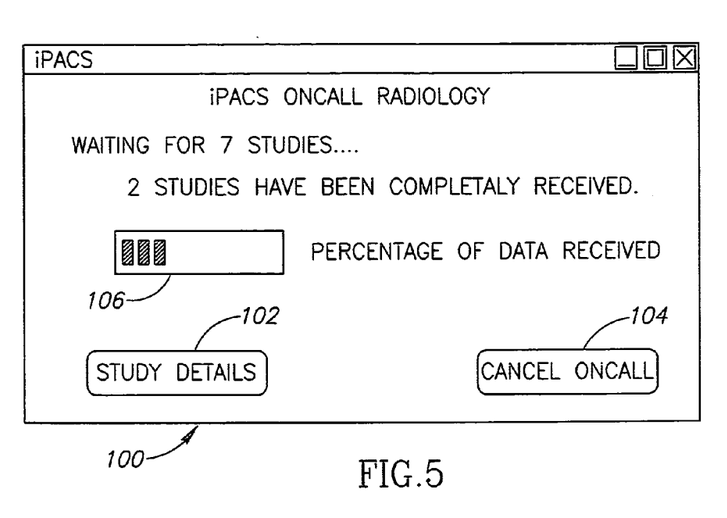
FIG. 5 is a diagram illustrating the OnCall window generated by the software of the present invention in response to a user clicking on the OnCall button.

A diagram illustrating the OnCall window generated by the software of the present invention in response to a user clicking on the OnCall button is shown in FIG. 5. The display window, generally referenced 100, includes a completion bar 106 indicating the percentage of data received so far by the client computer. The display 100 also indicates the total number of studies currently queued for transmission and the number of studies that have already been completely received. A Study Details button 102 is provided for users to display more details about the studies in the queue. A Cancel OnCall button 104 functions to cancel the automatic mode of operation (i.e. the OnCall mode in the iPACS example).

Figure 6:
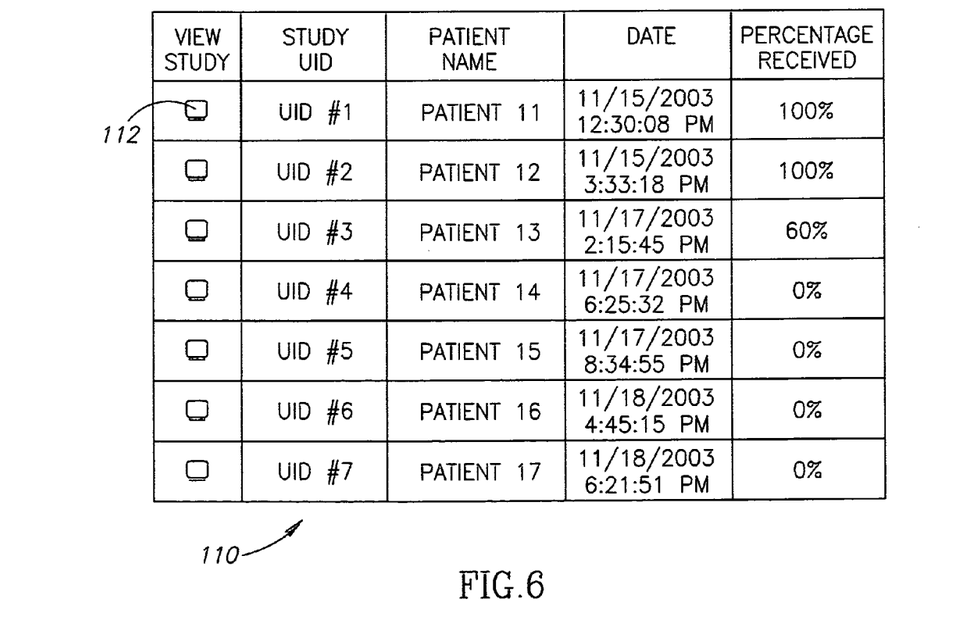
FIG. 6 is a diagram illustrating the details, including transmission status, of the studies that are currently queued on the publication server for transmission to client computers.

A diagram illustrating the details, including transmission status, of the studies that are currently queued on the publication server for transmission to client computers is shown in FIG. 6. The display window, generally referenced 110, shows more detailed information about each of the studies currently queued at the publication server for transmission to the client computer. The data shown for each study includes a View Study icon 112, study unique ID (UID), patient name, date and time of the study creation and percentage received indication.

In this example embodiment, the complete data for a study is transmitted before transmission of the next study in the queue begins. Referring to the sample display window 110, the first two studies (UID #1 and UID #2) have been completely received (i.e. 100%) while only 60% of the third study (UID #3) has been received. No data at all for the last four studies (UID #4, UID #5, UID #6 and UID #7) has been received as indicated by the 0% in the percentage received column of the table.

A key feature of the present invention is the ability of a user to immediately view the contents of a study regardless of the percentage of data received for that study at that point in time. A study can be immediately viewed by clicking on the View Study icon 112 for the particular study of interest. In response, a viewer window opens and the contents (e.g., images) of the study are displayed. Transmission of study data for the non-selected studies still continues but a higher priority is given to any requests for data of the selected study.

Depending on the viewer's zoom, pan, window level, etc. the viewer attempts to retrieve the data it needs to display the image accordingly. Since the data required may already have been received by the client computer, the client first searches in the local storage for the required data. If it is found, the data is read from the memory and used to display the image. If the required data is not found in the local storage (as would be the case if transmission for the selected study has not yet begun), then a request is generated and sent to the publication server. The publication server services the request, retrieves the data from the study storage 12 (FIG. 1) and transmits it to the requesting client computer for display to the user.

Another key feature of the present invention is the use of progressive image streaming techniques in sending study data from the publication server to client computers. A progressive image streaming technique suitable for use with the present invention is described in detail in U.S. Pat. No. 6,314,452 to Dekel et al., entitled "System and Method for Transmitting A Digital Image Over A Communication Network," incorporated herein by reference in its entirety.

In accordance with the invention, a progressive image streaming technique, such as described in U.S. Pat. No. 6,314,452, is utilized whereby entire images or image sequences do not need to be transferred from one location to another. Only the amount of data necessary according to the user's request and preference (i.e. zoom, pan, window level, etc.) are actually transmitted from the publication server computer to the client computer. The core of the progressive image streaming is designed in accordance with how the human eye processes information, delivering the most visually important information first. This allows extremely fast convergence to high quality allowing users to recognize important features of the study and begin working immediately (i.e. zooming, panning, window leveling, etc). Streaming eliminates lengthy image download times by rendering the key elements of the image first and then progressively and transparently adding image detail until the full data set has been completely presented.

Streaming only the region of interest (ROI) enables prioritized transmission of the currently viewed region of the image. Each time the user manipulates the image (zoom, pan, window level/width, etc.), newly requested data is streamed on the fly to the user's viewer application. This is done dynamically on any image without compressing or modifying it, yielding very high-speed efficiency. As a result, the user has the freedom to view any portion of the image, in any magnification, almost instantaneously. Similar prioritization is also applied to image sequence viewing (cine or stack mode), where users can begin working on an individual slice, without having to wait for the entire data set of slices to be streamed.

In accordance with the present invention, the automatic transmission of studies from the publication server to client computers may be performed using either push or pull functionality. In the case of push functionality, new studies that become available at the central storage site (i.e. study storage) are automatically sent to client computers over the communications network. The studies are sent according to a set of publication rules which governs which users are to receive which studies. In push mode, the publication server performs the publication rules check as each new study becomes available and 'pushes' the study data to users that are to receive it.

In the case of pull functionality, the client computer periodically polls the publication server for any new studies that have become available. The client computer performs the publication rule checking and issues the request to the publication server to send studies for users that meet the necessary criteria.

In either case, the main advantage of the automatic transmission of study data to a remote referring physician's client computer is that in many cases, the size of the image data within the study is relatively large and its transmission over a low bandwidth network (e.g., low speed dial-up lines) would take more than a few hours. It is thus advantageous to begin the transmission of study data as soon as possible in the hope that it will be transmitted in its entirety before the user at the client computer attempts to view it.

In accordance with the present invention, the automatic transmission of the study data is enhanced by adding a progressive functionality for use in cases where there is an immediate need to interact with the image data of the study before it is received in its entirety. The progressive functionality mechanism utilizes the real time progressive transmission capabilities of the imaging system described in U.S. Pat. No. 6,314,452 cited supra. For study data that includes image sequences such as CT or MRI slices, the invention may use the methods and mechanisms described in U.S. Publication No. US20030005140A1, to Dekel et al., published Jan. 2, 2003, entitled "Three-dimensional Image Streaming System and Method for Medical Images," incorporated herein by reference in its entirety. A lossless image streaming system for the transmission of images over a communication network that eliminates the necessity to store a compressed version of the original image by losslessly streaming ROI data using the original stored image that is suitable for use with the present invention is described in detail in U.S. Publication No. US20030059096A1, to Dekel et al., published Mar. 27, 2003, entitled "System and Method for the Lossless Progressive Streaming of Images Over A Communication Network," incorporated herein by reference in its entirety. Alternatively, the progressive streaming techniques described in the JPEG2000 standard may also be used with the invention.

When the user issues a command to view a particular study that was not completely received, the client computer switches from the automatic push or pull mode to a manual pull mode. In the manual pull mode, the publication server is requested to send study data using progressive image streaming techniques. In particular, the study data is sent in response to interactive ROI requests received from the client computer.

The methods of the publication imaging system operative on the client and server computers will now be presented. To aid in understanding the methods of the invention, the methods are described in the context of the iPACS software product and particularly the OnCall feature of the software. One skilled in relevant art can appreciate that the methods presented herein can be applied to other applications and specific software or hardware implements without departing from the scope of the invention.

Figure 7A:
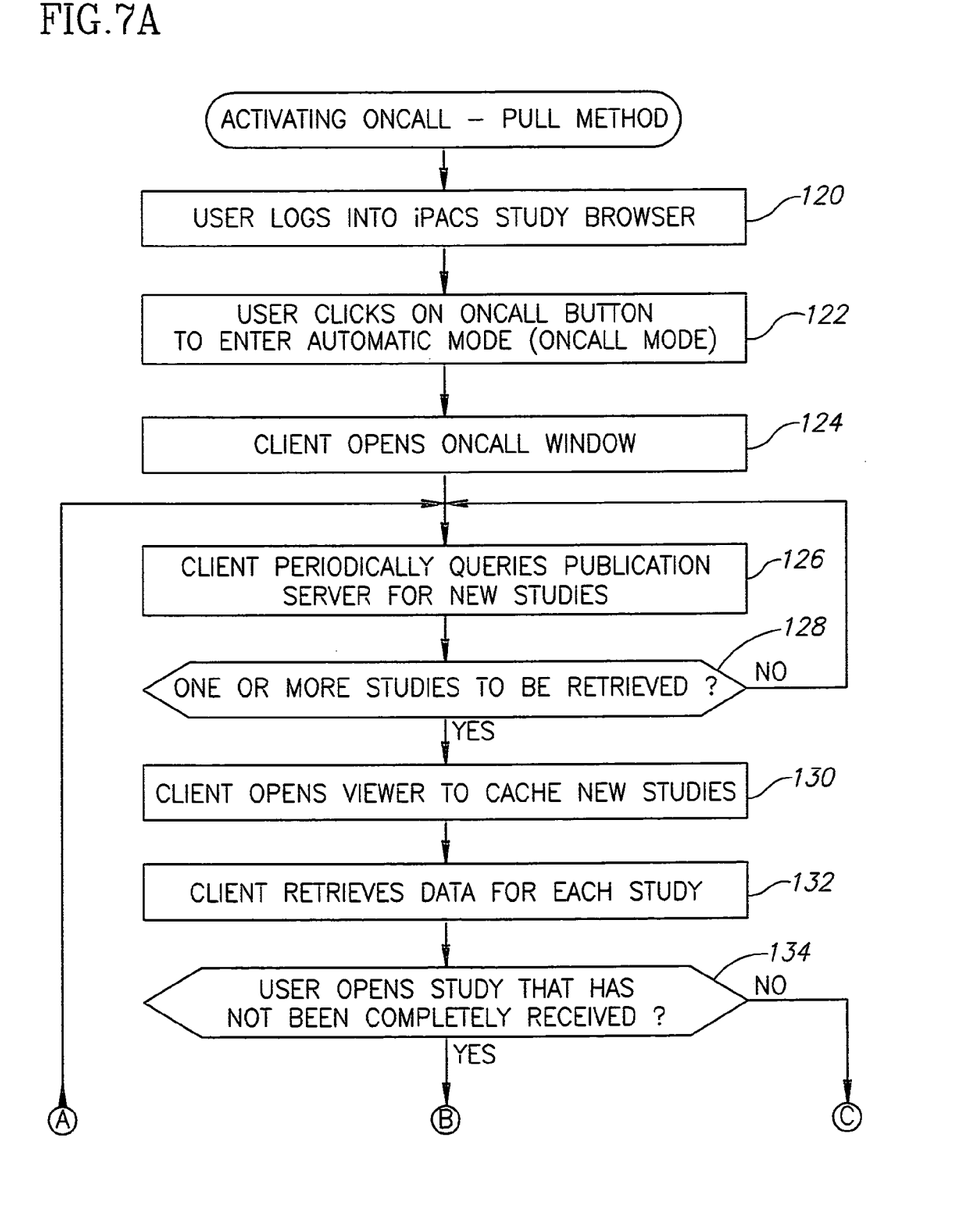
FIGS. 7A and 7B are a flow diagram illustrating a first method of activating the OnCall feature.
Figure 7B:
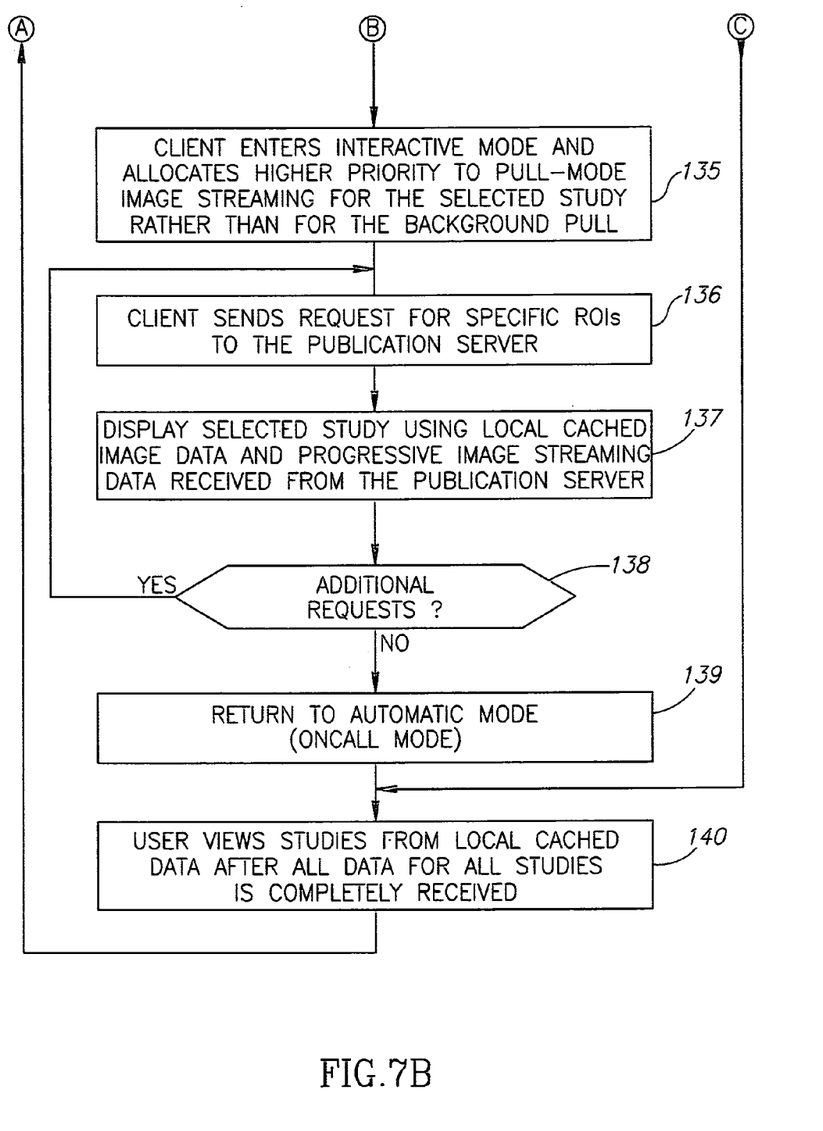

A flow diagram illustrating a first method of activating the OnCall feature using pull functionality is shown in FIGS. 7A and 7B. Initially, the user first logs into the iPACS study browser (step 120). This step logs the user into the publication server. A display window similar to that of FIG. 4 opens on the client computer. The user then clicks on the OnCall button to enter the automatic transmission mode or OnCall mode in this example (step 122). The client software opens the OnCall window (step 124). The display window shown at this point is similar to that shown in FIG. 5.

When the OnCall mode is entered, a new publishing rule is entered into the rule database that describes the source's location in the study storage hierarchy, the destination client(s) and the various filter parameters (e.g., patient name, modality, body part, etc.). The publishing rule may be created by the system administrator responsible for adding the details of new client destinations, changing users' permissions, etc. Alternatively, the publishing rule is created by end users having permission to request that new studies that meet certain specific criteria (i.e. parameters) that are added to the study storage be automatically forwarded to their client computer.

The client then begins periodically polling the publication server for new studies, e.g., every few minutes (step 126). If there are no new studies (step 128), the client continues to periodically poll the publication server and returns to step 126. If there are one or more new studies, the client computer checks using the publication rule database, whether the study should be pulled. If there are one or more studies that satisfy the rules and are to be retrieved (step 128), the client launches the viewer application to fetch and cache the new studies (step 130). The client then begins to retrieve data for each new study to be received (step 132).

Note that when a study is to be transmitted from the publication server to client computers, a transmission of the study contents (e.g., images) using progressive image streaming is initiated such that the information is sent in encoded layers of increasing accuracy and quality. Typically, the progressive image streaming occurs using a lossless mode whereby the accuracy of the data being sent increases in accuracy until lossless accuracy is achieved.

If the user opens a study for viewing whose data has not been completely received (step 134), the client computer enters interactive mode and initiates a viewing session. Higher priority is allocated to pull mode image streaming for the selected study than to the background data pull (step 135). In response to the user interacting with the image in the viewing session, one or more requests for regions of interest are generated and sent by the client computer to the publication server (step 136). The selected study is displayed using local cached study data (if any) and data received from the publication server using progressive image streaming techniques (step 137). The missing layers of accuracy for each region of interested (ROI) are requested by the client computer. In response, the publication server computer retrieves the requested data, encodes and transmits the corresponding data blocks to the client computer for subsequent display to the user.

If there are additional requests for ROIs (i.e. the user continues to interact with the image) (step 138), then the method continues with step 136 and requests the additional ROIs from the publication server. If there are no additional requests (i.e. user quits interactive mode) the system returns to automatic mode (i.e. OnCall mode) and retrieval of the queued studies continues (step 139). Any data already received by the client computer is used and does not need to be resent from the server.

If the user initiates a viewing session of a selected study after all the data has been completely received at the client computer (step 134), than the viewing session retrieves the data from the local cache without the need to subsequently pull any data from the publication server providing instant rendering of images (step 140). Once all the data for a study has been received, the images can be decodedand a pixel-by-pixel image is generated and stored in local storage.

Figure 8A:
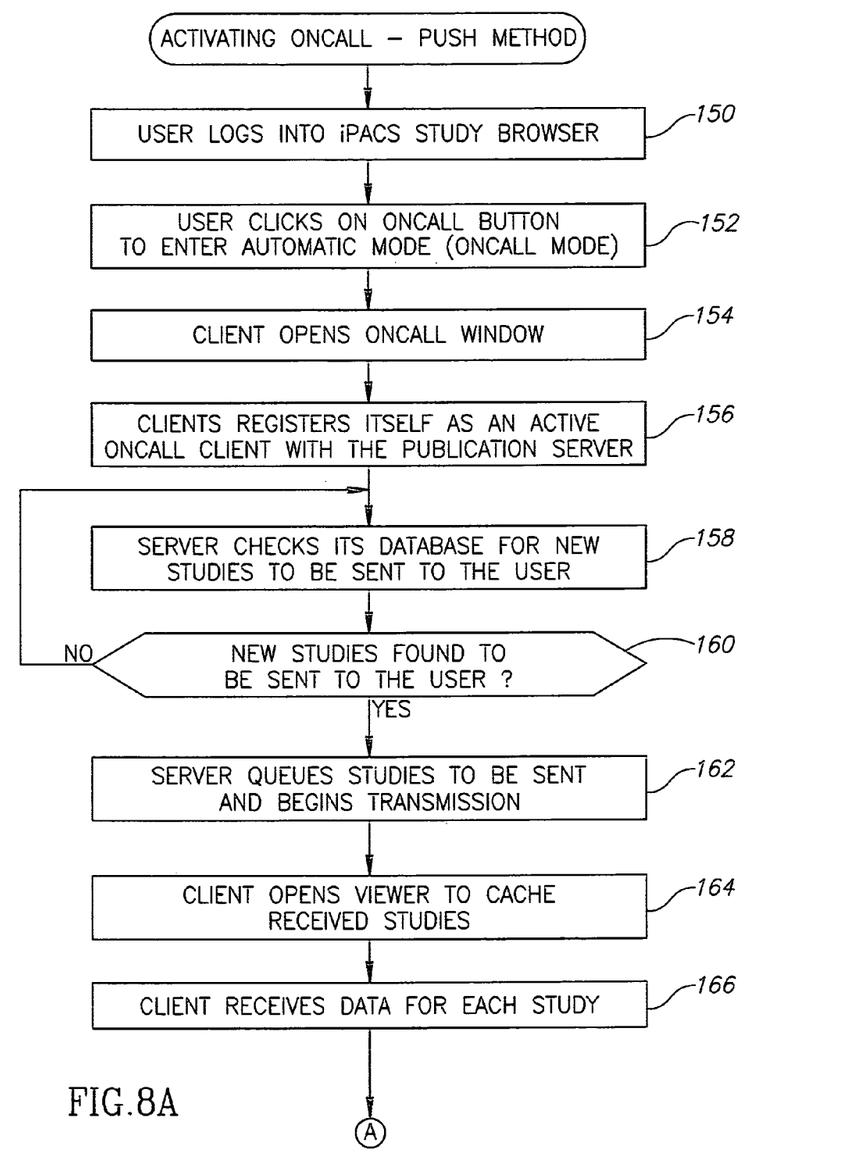
FIGS. 8A and 8B are a flow diagram illustrating a second method of activating the OnCall feature.
Figure 8B:
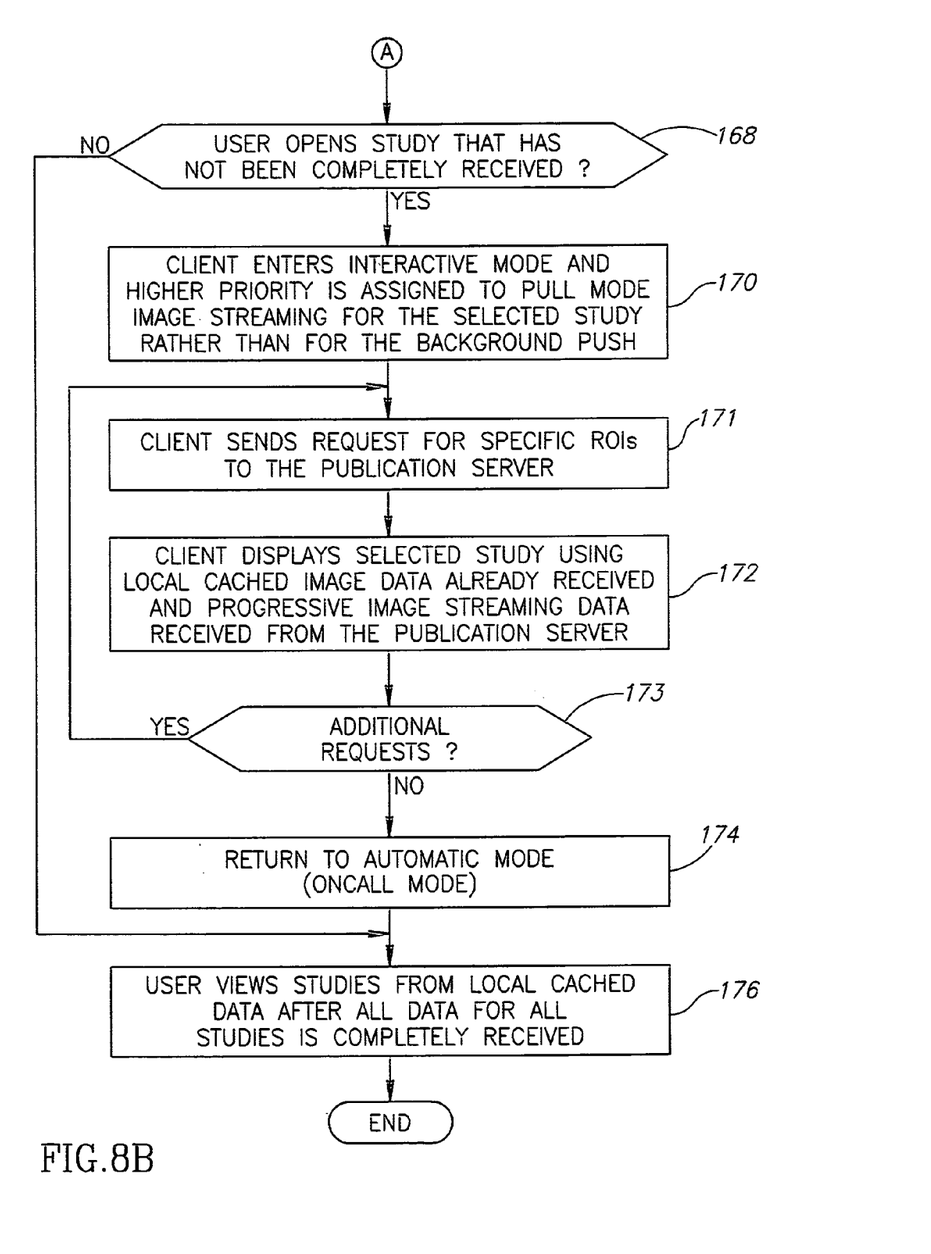

A flow diagram illustrating a second method of activating the OnCall feature using push functionality is shown in FIGS. 8A and 8B. This method is similar to that of the method of FIGS. 7A and 7B with the difference being that a push functionality is issued to automatically transmit new study data to client computers rather than pull functionality. Initially, the user first logs into the iPACS study browser (step 150). This step logs the user onto the publication server. A display window similar to that of FIG. 4 opens on the client computer. The user then clicks the OnCall button to enter the automatic transmission mode or OnCall mode in this example (step 152). The client software opens the OnCall window (step 154). The display window shown at this point is similar to that shown in FIG. 5.

When the OnCall mode is entered, the client computer registers itself as an active OnCall client at the publication server (step 156). A new publishing rule is entered into the rule database that describes the destination client(s) and the various filter parameters (e.g., patient name, modality, body part, storage hierarchy, etc.). The publishing rule may be created by the system administrator responsible for adding the details of new client destinations, changing users' permissions, etc. Alternatively, the publishing rule is created by end users having permission to request that new studies that meet certain specific criteria (i.e. parameters) that are added to the study storage be automatically forwarded to their client computer.

The publication server checks its study storage database for new studies that meet the publication rules criteria (step 158). If there are no new studies, the method returns to step 158 until a new study arrives. If there are one or more new studies that meet the publication rules criteria (step 160), the publication server queues the one or more studies to be sent and initiates progressive streaming of the study data (step 162). The client computer opens a viewer window to fetch and cache data received for the new studies (step 164). The client then begins to receive data for each new study (step 166). Note that when a study is to be transmitted from the publication server to client computers, a transmission of the study contents (e.g., images) using progressive image streaming is initiated such that the information is sent in encoded layers of increasing accuracy and quality. Typically, the progressive image streaming occurs using a lossless mode whereby the accuracy of the data being sent increased in accuracy until lossless accuracy is achieved.

If the user opens a study for viewing whose data has not been completely received (step 168), the client computer enters interactive mode and initiates a viewing session. Higher priority is assigned on the client computer and publication server to interactive image streaming of the selected study than to the background data push (step 170). In response to the user interacting with the image during the viewing session, one or more requests for regions of interest are generated and sent by the client computer to the publication server (step 171). The selected study is displayed using local cached study data (if any) and data received from the publication server using progressive image streaming techniques (step 172). The missing layers of accuracy for each region of interested (ROI) are requested by the client computer. In response, the publication server computer retrieves the requested data, encodes and transmits the corresponding data blocks to the client computer for subsequent display to the user.

If there are additional requests for ROIs (i.e. the user continues to interact with the image) (step 173), then the method continues with step 171 and requests the additional ROIs from the publication server. If there are no additional requests (i.e. user quits interactive mode) the system returns to automatic mode (i.e. OnCall mode) and retrieval of the queued studies continues (step 174). Any data already received by the client computer is used and does not need to be resent from the server.

If the user initiates a viewing session of a selected study after all the data has been completely received at the client computer (step 168), than the viewing session retrieves the data from the local cache without the need to subsequently pull any data from the publication server providing instant rendering of images (step 176).

It is important to note that in both the pull and push methods of activating the OnCall mode, the client/server protocol used to transmit study data is the same regardless of the mode of operation. The same client/server protocol (i.e. progressive image streaming) is used whether the system is in automatic publishing mode (i.e. OnCall) or in interactive viewing mode. It is the use of the same protocol for both automatic and interactive modes that enables a user to switch transparently back and forth between publishing mode and interactive mode at any time. When a study is selected for viewing in interactive mode, all data present in the client computer at that time is used to display the image. Any data retrieved during interactive mode is not retrieved again after switching back to automatic mode. Once automatic mode resumes, the process of retrieving study data for all queued studies continues. Any data already retrieved for a study while in interactive mode is utilized and does not need to be resent from the publication server.

Thus, the background task of retrieving study data for all queued studies continues regardless of the fact that the user may have switched to interactive mode. While in interactive mode, the data retrieval process continues while higher priority is given to any requests made by the user to view specific regions of interest of an image. Depending on several factors including available bandwidth, etc. the background data retrieval may be halted while the requests for ROIs are being handled. While no requests for additional specific ROIs are being made (such as while the physician is viewing and analyzing the image data already received) the background data retrieval task to transfer the remainder of the queued studies continues.

Figure 9:
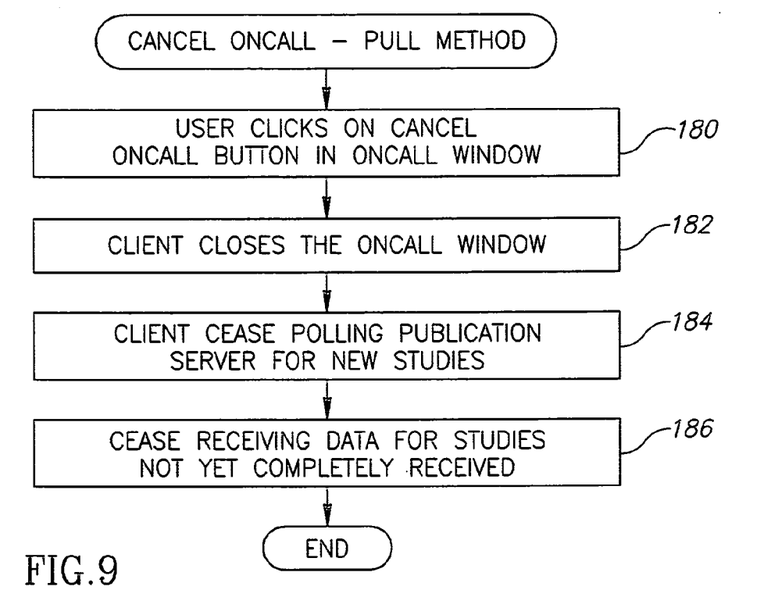
FIG. 9 is a flow diagram illustrating a first method of canceling the OnCall feature.

A flow diagram illustrating a first method of canceling the OnCall feature that uses pull functionality is shown in FIG. 9. Initially, the user clicks on the Cancel OnCall button 104 while the OnCall display window is open (FIG. 5) (step 180). In response to the button press, the client computer closes the OnCall window (step 182) and ceases periodic polling of the publication server for new studies (step 184). Data reception for any studies outstanding (i.e. data reception not complete) also ceases and operation of the client application returns to what it was before OnCall mode was entered (step 186).

Figure 10:
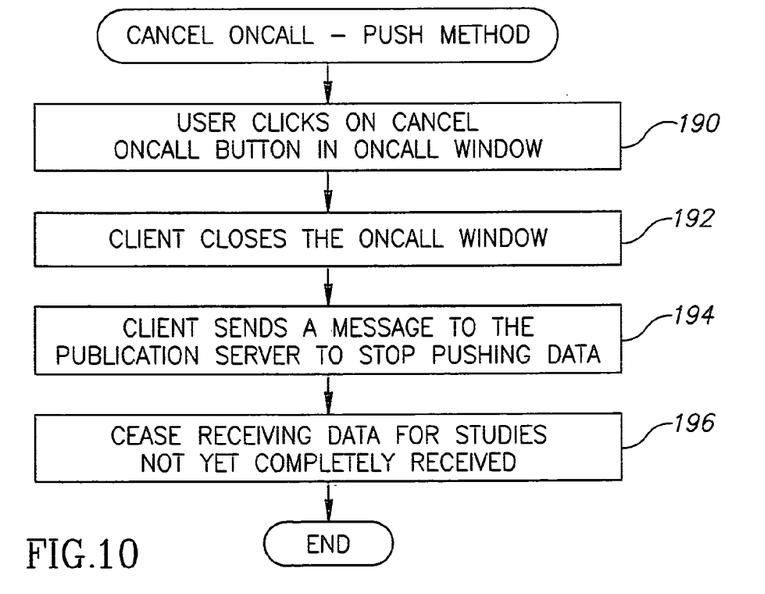
FIG. 10 is a flow diagram illustrating a second method of canceling the OnCall feature.

A flow diagram illustrating a second method of canceling the OnCall feature that uses push functionality is shown in FIG. 10. Initially, the user clicks on the Cancel OnCall button 104 while the OnCall display window is open (FIG. 5) (step 190). In response to the button press, the client computer closes the OnCall window (step 192). The client computer generates and sends a message to the publication server to cease pushing study data (step 194). Data reception for any studies outstanding (i.e. data reception not complete) ceases and operation of the client application returns to what it was before OnCall mode was entered (step 196).

Note that depending on the implementation, the cancellation of the OnCall mode may trigger a modification of the publication rules. In this case, a message containing the new parameters is sent to the publication server for entry into the publication rules database. Alternatively, the system administrator may also make modifications to the rules parameters.

It is intended that the appended claims cover all such features and advantages of the invention that fall within the spirit and scope of the present invention. As numerous modifications and changes will readily occur to those skilled in the art it is intended that the invention not be limited to the limited number of embodiments described herein. Accordingly, it will be appreciated that all suitable variations, modifications and equivalents may be resorted to, falling within the spirit and scope of the present invention.

What is claimed is:

1. A system for publishing studies over a communication network, comprising:
    a study storage device for storing a plurality of studies, each study comprising one or more images;
    a publication server coupled to said communications network, said publication server operative to enter an automatic publishing mode wherein one or more studies from among said plurality of studies are automatically sent to a client computer coupled to said communications network as they become available on said study storage device without any intervention by a user;
    said client computer comprising:
        means for receiving said one or more studies and storing them in a local cache;
        means for permitting the user to interrupt said automatic publishing mode at any time for a selected study that has not yet been received in its entirety from said publication server, and immediately entering an interactive mode whereby a dynamic interactive viewing session is initiated between the user and said publication server;
        means for streaming image data from said publication server to said client computer during said interactive viewing session using progressive image streaming techniques in response to requests for one or more regions of interest (ROI), said ROIs corresponding to specific portions of an image as determined by the user's current viewing parameters and preferences, wherein said progressive image streaming techniques utilize compression to transmit said ROI image data in encoded layers of increasing accuracy and quality whereby the most visually important image data is streamed first;
        wherein a search for requested ROI image data is first performed on said local cache, and only if not found, said requested ROI image data is streamed by said publication server to said client computer; and
        wherein transmission of ROI image data from said publication server during said interactive mode for said selected study is given higher priority over transmission of study data of non-selected studies which continues at lower priority.

2. The system according to claim 1, wherein said publication server is adapted to send said one or more studies to said client computer in accordance with a set of publication rules.

3. The system according to claim 2, wherein said publication rules comprise instructions for determining, for each new study, which clients are to receive it.

4. The system according to claim 1, wherein said client computer comprises means for using only required data stored in said local storage when said user initiates a viewing session of said selected study after all said required data for said selected study is completely received.

5. The system according to claim 1, wherein said client computer comprises means for using progressive image streaming techniques to retrieve data from said publication server for said selected study when said user initiates a viewing session of said selected study before any data corresponding thereto has been received by said client computer.

6. The system according to claim 1, wherein said client computer comprises data pull means adapted to periodically poll said publication server for new studies that have not yet been retrieved.

7. The system according to claim 1, wherein said client computer comprises data push means adapted to configure said publication server to automatically check for and send new studies that have not yet been transmitted to said client.

8. The system according to claim 1, wherein said publication server is adapted to send said one or more studies to said client using progressive image streaming techniques whereby information is sent in encoded layers wherein each successive layer has higher accuracy and quality than the layer previous thereto.

9. The system according to claim 1, wherein said client computer comprises means whereby if said user initiates a viewing session of said selected study after data is completely received by said client, then said client utilizes said data to provide instant rendering of images within said selected study.

10. The system according to claim 1, farther comprising means for permitting said user to freely switch back and forth between automatic mode and interactive mode without the need to switch protocols.

11. The system according to claim 1, wherein said progressive image streaming techniques are performed utilizing JPEG2000 standard.

12. An image publication system for use on a client computer coupled to a communications network, comprising:
- first means for entering an automatic publishing mode whereby new studies are sent automatically from a publication server to said client computer over said communications network as they become available without requiring any intervention by a user;
- a local cache for storing said studies;
- second means for receiving said studies and storing them in said local cache;
- third means for permitting the user to interrupt said automatic publishing mode at any time for a selected study that has not yet been received in its entirety from said publication server, and immediately entering an interactive mode whereby a dynamic interactive viewing session is initiated between the user and said publication server;
- fourth means for streaming image data from said publication server to said client computer during said interactive viewing session using progressive image streaming techniques in response to requests for one or more regions of interest (ROI), said ROIs corresponding to specific portions of an image as determined by the user's current viewing parameters and preferences, wherein said progressive image streaming techniques utilize compression to transmit said ROI image data in encoded layers of increasing accuracy and quality whereby the most visually important image data is streamed first;
- wherein a search for requested ROI image data is first performed on said local cache, and only if not found, said requested ROI image data is streamed by said publication server to said client computer;
- wherein transmission of ROI image data from said publication server during said interactive mode for said selected study is given higher priority over transmission of study data of non-selected studies which continues at lower priority; and
- fifth means for decoding and displaying data received from said publication server in response to said requests for one or more ROIs.

13. The system according to claim 12, wherein said publication server is adapted to send said studies to said client computer in accordance with a set of publication rules.

14. The system according to claim 12, wherein said publication server is adapted to send said studies while in said automatic mode using progressive image streaming techniques whereby information is sent in encoded layers wherein each successive layer has higher accuracy and quality than the layer previous thereto.

15. The system according to claim 12, wherein said client computer comprises means for using only data stored in said local cache when a user initiates a viewing session of said selected study after all data for said selected study is completely received.

16. The system according to claim 12, wherein said client computer comprises means for using progressive image streaming techniques to retrieve data from said publication server for said selected study when a user initiates a viewing session of said selected study before any data corresponding thereto has been received by said client computer.

17. The system according to claim 12, wherein said client computer comprises data pull means adapted to periodically poll said publication server for new studies that have not yet been retrieved.

18. The system according to claim 12, wherein said client computer comprises data push means adapted to configure said publication server to automatically check for and send new studies that have not yet been transmitted to said client.

19. The system according to claim 12, wherein said publication server is adapted to send said one or more studies to said client while in interactive mode using progressive image streaming techniques whereby information is sent in encoded layers wherein each successive layer has higher accuracy and quality than the layer previous thereto.

20. The system according to claim 12, wherein said client computer comprises means whereby when said user initiates a viewing session of said selected study after data is completely received by said client, then said client utilizes said data to provide instant rendering of images within said selected study.

21. The system according to claim 12, further comprising means for permitting said user to freely switch back and forth between said automatic mode and said interactive mode without the need to switch protocols.

22. The system according to claim 12, wherein said progressive image streaming techniques are performed utilizing JPEG2000 standard.

23. An image publication system for use on a publication server computer coupled to a communications network, comprising:
- first means for configuring said publication server computer in an automatic publishing mode in response to a command received from a client computer coupled to said communications network whereby new studies are automatically sent to said client computer as they become available without requiring any intervention by a user;
- second means for halting said automatic publishing mode at any time for a selected study that has not yet been transmitted in its entirety to said client computer, and immediately entering an interactive mode whereby a dynamic interactive viewing session is initiated between a user and said publication server computer;
- third means for streaming image data from said publication server computer to said client computer during said interactive viewing session using progressive image streaming techniques in response to requests from said client computer for one or more regions of interest (ROI), said ROIs corresponding to specific portions of an image as determined by the user's current viewing parameters and preferences, wherein said progressive image streaming techniques utilize compression to transmit said ROI image data in encoded layers of increasing accuracy and quality whereby the most visually important image data is streamed first;
- wherein said requested ROI image data is streamed by said publication server to said client computer only if said requested ROI image data is not found during a search of local cache on said client computer; and
- wherein transmission of ROI image data from said publication server during said interactive mode for said selected study is given higher priority over transmission of study data of non-selected studies which continues at lower priority.

24. The system according to claim 23, wherein said publication server computer is adapted to send said one or more studies to said client computer using progressive image streaming techniques whereby information is sent in encoded layers wherein each successive layer has higher accuracy and quality than the layer previous thereto.

25. The system according to claim 24, wherein said progressive image streaming techniques are performed utilizing JPEG2000 standard.

26. The system according to claim 23, wherein said publication server computer is adapted to send one or more of said new studies to said client computer in accordance with a set of publication rules.

27. A computer program product for use in a client computer coupled to a communication network, said computer program product comprising:

a computer readable medium having computer readable program code means embodied in said medium for receiving and displaying studies from a publication server coupled to said communications network, said computer program product comprising:

computer readable program code means for entering an automatic publishing mode whereby new studies are sent automatically from said publication server to said client computer over said communications network as they become available without requiring any intervention by a user;

computer readable program code means for receiving said studies and storing them in a local cache;

computer readable program code means for permitting the user to interrupt said automatic publishing mode at any time for a selected study that has not yet been received in its entirety from said publication server, and immediately entering an interactive mode whereby a dynamic interactive viewing session is initiated between the user and said publication server computer readable program code means for streaming image data from said publication server to said client computer during said interactive viewing session using progressive image streaming techniques in response to requests for one or more regions of interest (ROI), said ROIs corresponding to specific portions of an image as determined by the user's current viewing parameters and preferences, wherein said progressive image streaming techniques utilize compression to transmit said ROI image data in encoded layers of increasing accuracy and quality whereby the most visually important image data is streamed first, wherein a search for requested ROI image data is first performed on said local cache, and only if not found, said requested ROI image data is streamed by said publication server to said client computer, wherein transmission of ROI image data from said publication server during said interactive mode for said selected study is given higher priority over transmission of study data of non-selected studies which continues at lower priority; and computer readable program code means for decoding data received from said publication server in response to requests for one or more ROIs.

28. A computer program product for use in a publication server computer coupled to a communication network, said computer program product comprising:

a computer readable medium having computer readable program code means embodied in said medium for publishing studies to a client computer coupled to said communications network, said computer program product comprising:

computer readable program code means for configuring said publication server computer in an automatic publishing mode in response to a command received from a client computer coupled to said communications network whereby new studies are automatically sent to said client computer as they become available without requiring any intervention by a user;

computer readable program code means for halting said automatic publishing mode at any time for a selected study that has not yet been transmitted in its entirety to said client computer, and immediately entering an interactive mode whereby a dynamic interactive viewing session is initiated between a user and said publication server computer; and computer readable program code means for streaming image data from said publication server computer to said client computer during said interactive viewing session using progressive image streaming techniques in response to requests from said client computer for one or more regions of interest (ROI), said ROIs corresponding to specific portions of an image as determined by the user's current viewing parameters and preferences, wherein said progressive image streaming techniques utilize compression to transmit said ROI image data in encoded layers of increasing accuracy and quality whereby the most visually important image data is streamed first, wherein said requested ROI image data is streamed by said publication server to said client computer only if said requested ROI image data is not found during a search of local cache on said client computer, wherein transmission of ROI image data from said publication server during said interactive mode for said selected study is given higher priority over transmission of study data of non-selected studies which continues at lower priority.

* * * * *